United States Patent [19]

Genshaw et al.

[11] Patent Number: 5,182,213
[45] Date of Patent: Jan. 26, 1993

[54] METHOD FOR DETECTING THE PRESENCE OF PEROXIDATIVELY ACTIVE SUBSTANCE IN BASIC MEDIA

[75] Inventors: Marvin A. Genshaw, Elkhart; Michael J. Pugia, Granger, both of Ind.

[73] Assignee: Miles Inc., Elkhart, Ind.

[21] Appl. No.: 670,730

[22] Filed: Mar. 18, 1991

[51] Int. Cl.$^5$ ............................................. G01N 33/72
[52] U.S. Cl. ....................................... 436/66; 435/28; 422/56
[58] Field of Search ...................... 436/66; 435/14, 28, 435/74; 422/55, 56

[56] References Cited

U.S. PATENT DOCUMENTS

| | | | |
|---|---|---|---|
| 3,986,833 | 10/1976 | Mast et al. | 436/66 |
| 4,278,439 | 7/1981 | White | 436/66 |
| 4,295,853 | 10/1981 | Kasahara et al. | 436/66 |
| 4,447,542 | 5/1984 | Gantzer | 436/66 |
| 4,587,220 | 5/1986 | Mayambala-Mwanika et al. | 436/66 |
| 4,615,972 | 10/1986 | Gallacher | 435/28 |
| 4,800,167 | 1/1989 | Bailey et al. | 436/66 |
| 4,855,229 | 8/1989 | Kogure et al. | 435/28 |
| 5,089,420 | 2/1992 | Albarella et al. | 436/66 |

FOREIGN PATENT DOCUMENTS 253548A  1/1988  European Pat. Off. .

OTHER PUBLICATIONS

Clinical Chemistry Principles and Techniques, 2nd ed. Harper & Row, pp. 1124–1125 (1974).
H. Yamamoto et al., Catalytic Actions of Synthetic Polypeptides, 2 . . . Int. J. Biol. Macromol., 4, 116–120 (1982).

Primary Examiner—James C. Housel
Assistant Examiner—Mihon I. Cano
Attorney, Agent, or Firm—Jerome L. Jeffers

[57] ABSTRACT

An assay for the detection of a peroxidatively active substance in a test sample. The assay employs a phenylenediamine and a naphthol which, under the conditions of the assay, couple to form a chromogen thereby indicating the presence of the analyte. The assay is carried out at a pH of from 10 to 14 since false positives due to ascorbate interference are minimized in highly alkaline media.

7 Claims, No Drawings

METHOD FOR DETECTING THE PRESENCE OF PEROXIDATIVELY ACTIVE SUBSTANCE IN BASIC MEDIA

BACKGROUND OF THE INVENTION

The present invention relates to a composition, device and method for determining the presence or concentration of a peroxidatively active substance in a test sample. More particularly, the present invention relates to a new and improved method of assaying a liquid test sample such as urine for a peroxidatively active substance, e.g. occult blood, by utilizing a reduction resistant indicator reagent composition. The indicator reagent composition, in a wet phase assay or a dry phase assay, undergoes a detectable or measurable response upon contact with a test sample containing a peroxidatively active substance.

Peroxidase is an enzyme that catalyzes the oxidation of various compounds, such as phenols and amines, by peroxides. In addition, particular compounds have been termed pseudoperoxidases because they behave in a manner similar to the peroxidase enzyme. Pseudoperoxides liberate oxygen from hydroperoxides creating an oxidant capable of accepting an electron from a donor species. Accordingly, the pseudoperoxidases are enzyme like in that they catalyze, or otherwise participate in, reactions between peroxides and oxidizable compounds. The pseudoperoxidases, which include hemoglobin and its derivatives, are also termed peroxidatively active substances. For example, a peroxidatively active substance, such as hemoglobin and its derivatives, catalyzes the interaction between a hydroperoxide and an oxidizable dye. In such interactions, the peroxidatively active substance imitates the peroxidase enzyme and catalyzes or otherwise participates in an interaction between the oxidizable dye and the peroxide. The oxygen transferred from a peroxide to a peroxidatively active substance creates an oxidant capable of accepting an electron from an oxidizable dye. The resulting interaction provides a detectable response, such as a color transition, wherein the intensity of the response is indicative of the presence or the concentration of the peroxidatively active substance.

Assays for a peroxidatively active substance are based upon the above described chromogenic interaction, wherein the degree and intensity of the color transition of the indicator dye are correlated to the concentration of the peroxidatively active substance in the test sample. Assays for a peroxidatively active substance are particularly useful in detecting and measuring low concentrations of blood, often termed "occult" blood, in body fluid samples such as urine, feces or gastrointestinal contents. Although occult blood is not visible to the naked eye, its detection is important in the diagnosis of hemorrhages in the stomach, intestines and urinary tract. The hemorrhages are caused, for example, by tumors, ulcers or inflammations of the organ in question. Presently, most methods of determining the presence of occult blood in a test sample are based upon the pseudoperoxidase activity of hemoglobin.

Myoglobin, the red respiratory pigment of muscle tissue, is another peroxidatively active substance. Myoglobin is very similar to hemoglobin in its composition and chemical reactions. Myoglobin can be liberated from muscle cells by certain types of injury, and in such cases, the myoglobin will circulate in the plasma and be excreted in the urine. In addition, certain genetic muscle disorders can cause the muscles to lose myoglobin that subsequently appears in the urine. Myoglobin also is found in the urine after a cardiac infarct. Other peroxidatively active substances are also present in leukocytes and bacteria, and, in general, the detection of a peroxidatively active substance is especially important in the diagnosis of diseases and infections of the kidneys and urinary tract. Accordingly, accurate and thorough assays of urine and other test samples for peroxidatively active substances must be available for both laboratory and home use. The assays must permit the detection and measurement of the peroxidatively active substance such that a correct diagnosis can be made and correct medical treatment implemented, monitored and maintained.

It is advantageous for the assay method for a peroxidatively active substance to be suitable for use both in wet phase assays and in dry phase reagent strips for the rapid, economical and accurate determination of a peroxidatively active substance in urine or other test sample. Methods based on dip-and-read dry phase test strips have proven especially useful because dry phase test strip methods are readily automated and provide reproducible and accurate results. Some test strips used in assays for peroxidatively active substances have a single test area consisting of a small square pad of a suitable carrier matrix impregnated with an indicator reagent composition comprising an indicator chromogen, such as a benzidine dye; a hydroperoxide; and a buffer. The assay for a peroxidatively active substance in urine is performed by dipping the colorimetric test strip into a well mixed, uncentrifuged urine sample and then comparing the resulting color of the test area of the strip to a standardized color chart provided with the test strip container. Such occult blood tests are usually included on multideterminant reagent strips to screen urine samples during routine physical examinations since it is important to detect a bleeding condition in the urinary tract at an early stage in its development.

The test for peroxidatively active substances described above is complicated by the presence of ascorbate since this ion is a strong reducing agent which can transfer an electron to the oxidized indicator resulting in false negative results. The inclusion of certain metal ion complexes, such as Fe-HEDTA, in the indicator reagent composition essentially eliminates ascorbate interference, however, the metal ion complexes also demonstrate peroxidase activity thereby catalyzing the color-forming reaction between the peroxide and the oxidizable dye which can, under some circumstances, result in false positives or erroneously high assay results due to additional dye oxidation mediated by the metal ion complex.

The prior art contains numerous references to the wet and dry phase chemistry which can be utilized in assaying fluids for peroxidatively active substances. For example, a wet chemistry assay for a peroxidatively active substance in an acidic medium is presented in R. M. Henry et al., *Clinical Chemistry Principles and Techniques*, 2nd ed., Harper & Row, pp. 1124–1125 (1974). This wet phase assay procedure employs glacial acetic acid as a buffer, diphenylamine as an indicator dye and hydrogen peroxide. The preferred method of assaying for a peroxidatively active substance involves the use of a dry phase test strip. This is because the test strip format is easier to use in that it requires neither the continual preparation of reagents nor the attendant apparatus.

U.S. Pat. No. 4,587,220 discloses the use of a chelated ferric ion to eliminate ascorbic acid and ascorbate ion interference in an assay for a peroxidatively active substance. This is accomplished by first incorporating a ferric chelate, such as the ferric chelate of N-(2-hydroxyethyl)ethylenediaminetriacetic acid (Fe-HEDTA), into the carrier matrix of a test device. Then, after drying, the indicator dye is incorporated into the carrier matrix. This two-step method of preparing the test device provides an ascorbate resistant test pad that also demonstrates a sufficient stability to resist a false positive assay result during storage.

Yamamoto et al., Int. J. Biol. Macromol., 4, 116-120 (1982) discuss a reduction of ascorbate concentration through auto-oxidation at high pH.

Published European patent application 0253548 describes a liquid composition for determining occult blood with a water-miscible aprotic solvent, water, a chelating agent, a stabilizer, an organic peroxide and an indicator which may be a tetramethylbenzidine derivative or tetramethyl-p-phenylenediamine at a preferred pH range of 10 to 11.

The present invention employs a coupled indicator system that operates at a pH of 10-14 (preferably 12-14) where ascorbate auto-oxidation and/or metal catalyzed oxidation occur at a faster rate thereby tending to reduce ascorbate interference.

In co-pending U.S. application Ser. No. 468,665 there is disclosed an assay for manganese which involves the use of a porphyrin for chelation of the Mn ion and a redox indicator which provides a detectable response when oxidized by oxygen. Suitable redox indicators include a phenylenediamine as developer and a napthol as coupler. A peroxide is not included in this assay thereby reducing potential interference caused by peroxidases in the blood sample being analyzed.

SUMMARY OF THE INVENTION

The present invention is directed to a method of assaying a test sample for a peroxidatively active substance by contacting the test sample, at a pH of from 10-14, with a reagent composition comprising a peroxide and a phenylenediamine and a napthol which, under the conditions of the assay, couple to form a chromogen due to the transfer of an electron from the peroxidatively active substance which has been activated by its having come into contact with the peroxide.

Also included within the scope of the invention is a reagent system comprising a peroxide, a phenylenediamine, a napthol and a buffer which is suitable for maintaining the reagent at a pH of from 10-14 when it is contacted with an aqueous test sample.

The reagent system may be incorporated into a suitable carrier matrix for example a bibulous material such as filter paper or a nonbibulous material such as a strip, layer or membrane of a polymerized substance or a combination thereof.

DESCRIPTION OF THE INVENTION

A commercially useful urine assay for occult blood must be stable, sensitive and resistant to ascorbic acid interference. The method and device of the present invention accurately assay for a low concentration of a peroxidatively active substance in fluids such as urine. The assay composition used in the present method and device is stable, resists ascorbate interference and undergoes a color transition only in response to the concentration of the peroxidatively active substance in the test sample thereby providing a sensitive and reliable assay.

Furthermore, the method and device of the present invention can be used to determine the presence or quantitative concentration of a peroxidatively active substance in blood plasma or serum, feces, and gastrointestinal contents as well as many other biological fluids and semisolids.

The chromogenic indicator useful in the present invention comprises a phenylenediamine as developer and a napthol as the coupler therefore. In general, the developer is selected from those phenylenediamines of the formula:

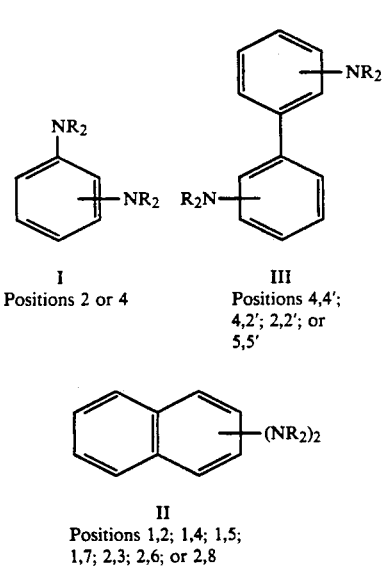

I
Positions 2 or 4

III
Positions 4,4'; 4,2'; 2,2'; or 5,5'

II
Positions 1,2; 1,4; 1,5; 1,7; 2,3; 2,6; or 2,8

Where R is H, $CH_3$, $CH_2CH_3$, $CH_2CH_2OH$, $C_6H_5$, $CH_2CH_2CH_3$ (or any combination).

In addition, the aromatic rings can be substituted with any number of X groups where X is H, Cl, $NO_2$, Br, I, Fl, CN, $CH_3$, $CH_2CH_3$, $CH_2CH_2CH_3$, $OCH_3$, $OCH_2CH_3$, $C_6H_5$ (or any combination).

Particular phenylene diamines according to structures I, II and III that are suitable for use in the present invention are:

Structure I: bis-hydroxyethyl-1,4-phenylenediamine; 1,2-phenylenediamine, 1,4-phenylenediamine hydrochloride; 3-nitro-1,2-phenylenediamine; 4-nitro-1,2-phenylenediamine; 4-methoxy-1,2-phenylenediamine; 2-chloro-1,4-phenylenediamine sulfate; 2-ethoxy-1,4-phenylenediamine; N,N-dimethyl-1,4-phenylenediamine; 2,3-dimethyl-1,4-phenylenediamine; 4,5-dimethyl-1,2-phenylenediamine; N,N-diethyl-1,4-phenylenediamine dihydrochloride; N-phenyl-1,4-phenylenediamine; N,N,N',N'-tetramethyl-1,4-phenylenediamine; N-methyl-N'-hydroxyethyl-1,4phenylenediamine; and 2,3,5,6-tetramethyl-1,4phenylenediamine. 3,3',5,5'-tetramethyl-benzidine; 2,2'-dimethyl-biphenyl-4,4'-diamine; 3,3'-diaminobenzidine-tetrahydrochloride; and N,N,N',N'-tetramethyl-biphenyl-4,4'-diamine. N,N-dimethyl-1,4-naphthyldiamine; 1,4-naphthyldiamine; 1,5-diaminonaphthaline; 1,8-diamino naphthalene; 2,3-diaminonaphthalene; 5-chloro-1,4-naphthyldiamine and 1-ethoxy-2,3-diaminonaphthalene.

The coupler has the formula:

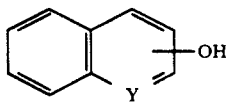

Where Y is CH, S, O or N and is not limited to a specific position within the aromatic ring. In addition, the aromatic rings can be substituted with any number of X groups where X is H, Cl, Br, I, Fl, CN, $CH_3$, $CH_2CH_3$, $CH_2CH_2CH_3$, $OCH_3$, $OCH_2CH_3$, $SO_3H$, $CO_2H$, $PO_3H$, $C_6H_5$ or any combination thereof.

Particular naphthols suitable for use in the present invention include 2-methoxy-1-naphthol; 2-methyl-1-naphthol; 1-naphthol, 2-naphthol, 4-chloro-1-naphthol; 1-bromo-2-naphthol; 6-bromo-2-naphthol; 1,6-dibromo-2-naphthol; 2,4-dichloro-1-naphthol; 6-methyl-2-naphthol; 1-methoxy-2-naphthol; 2-phenyl-1-naphthol; 1-hydroxy quinoline, 5-hydroxy quinoline; 3-hydroxy-1-methyl-quinoline; 6-hydroxy quinoline; 2-hydroxy quinoline, 8-hydroxy-quinoline-5-sulfonic acid; 1-naphthol-4-carboxylic acid; 8-hydroxyl-5-nitroquinoline; 5-chloro-8-hydroxyquinoline and 4-ethyl-1-naphthol.

The concentration of the phenylenediamine developer in the reagent composition will normally range from about 1 mM to about 100 mM, preferably from 10 to 50 mM and that of the naphthol coupler from about 1 mM to about 100 mM, preferably from 10 to 50 mM. When incorporated into a suitable carrier matrix, the developer and coupler are normally present in an amount of from 100 to 10,000 mg/m². Preferred concentrations range from 1,000 to 5,000 mg/m².

In addition to the phenylenediamine developer and naphthol coupler, the reagent composition also includes a hydroperoxide capable of liberating free oxygen when brought in contact with the peroxidatively active substance. The peroxidatively active substance present in the test sample catalyzes the liberation of free oxygen from the hydroperoxide and transfers the free oxygen to the indicator dye, thereby initiating the color transition of the developer/coupler combination. A suitable hydroperoxide should be sufficiently stable such that free oxygen is not liberated in the absence of a peroxidatively active substance and should possess a sufficiently low vapor pressure such that it does not evaporate or sublime from the reagent composition during storage or after it is incorporated into a carrier matrix of a dry phase test strip. Furthermore, when the reagent composition is to be used in the assay of urine for occult blood, the hydroperoxide should demonstrate a sufficient sensitivity to detect 1 part of hemoglobin in one million parts of the test sample. Suitable hydroperoxides include cumene hydroperoxide, t-butyl hydroperoxide, diisopropylbenzene hydroperoxide, 1-hydroxycyclohexane-1-hydroperoxide, 2,5-dimethylhexane-2,5-dihydroperoxide, paramenthane hydroperoxide, 1,4 diisopropyl monohydroperoxide, p-t-butylisopropylbenzene hydroperoxide, 2-(α-hydroperoxyisopropyl)-6-isopropylnaphthalene, tetralin hydroperoxide and combinations thereof. In the assay of urine for occult blood, 1,4-diisopropylbenzene dihydroperoxide (DBDH) is the preferred hydroperoxide because of its stability, sensitivity and non-volatility.

The concentration of hydroperoxide in the indicator reagent composition will normally range from about 1 mM to about 100 mM, and from 100 to 10,000 mg/m² in the matrix format. Preferred concentrations range from 25 to 75 mM and 2,500 to 7,500 mg/m². The specific amount of a particular hydroperoxide included in the composition is dependent upon the physical and chemical properties of the particular hydroperoxide such as stability and its sensitivity towards the peroxidatively active substance being assayed.

While the invention is not to be limited to any particular theory or mechanism of action, it is believed that the peroxidase is activated through oxidation by the hydroperoxide to a species capable of oxidizing the phenylenediamine substrate which in turn couples with the naphthol coupling agent to form a chromogen. The color change can be visibly detected or determined spectrophotometrically.

This technique is particularly effective at a pH in the range of from about 10 to about 14 and preferably at a pH of from 12 to 14. In a wet system, the appropriate pH can be achieved by running the assay in a 0.1N NaOH solution. When the assay system is to be used in a dry reagent strip format, a buffer is added to maintain the pH in the desired range. Suitable buffers include glycine, N,N'-Bis (3-sulfopropyl) ethylene diamine, 3-aminopropane sulfonic acid, carbonate, piperidine, phosphate, aspartic acid, alanine, 3-cyclohexylamino propane sulfonic acid, alkyl amines such as triethyl amine, guanidine and guanidine derivatives such as creatine and phenol.

The assay system of the present invention is also well suited for use with alkaline oxidases. Such enzyme systems include amino acid oxidase, galactose oxidase, polyphenol oxidase, plasma amine oxidase, 1-tryptophan peroxidase, uricase and xanthine oxidase. For example uricase activity can be measured using the present assay provided that a uric acid substrate is present for the uricase to act on. Conversely, uric acid could be measured provided that uricase enzyme was present. Thus, for example, in the presence of a substrate and alkaline oxidase, hydrogen peroxide is generated (reaction 1) and hydrogen peroxide is detected using peroxidase and the coupled indicator system (reaction 2).

(Reaction 1)

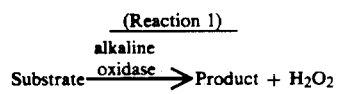

(Reaction 2)

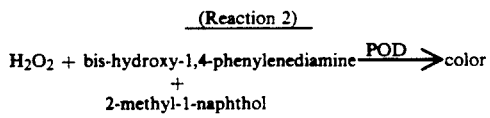

Substrates, alkaline oxidases active in basic medium and the products they produce are represented by the following examples.

| Substrate | Alkaline Oxidase | Product |
| --- | --- | --- |
| D-alanine | D-aminoacid oxidase | pyruvate |
| galactose | galactose oxidase | galactonic acid |
| L-tyrosine | polyphenyl oxidase | 4-hydroxyphenyl pyruvate |
| putrescine | plasma amine oxidase | 1-diamine-4-butanaldehyde |
| L-tryptophan | 1-tryptophan peroxidase | indole |
| uric acid | uricase | allantoin |
| xanthine | xanthine oxidase | uric acid |

The method of practicing the present invention is further illustrated by the following examples in which the wavelength at which the maximum absorbance occurred was selected for each indicator/solvent system.

EXAMPLE I

The following solutions were made:
1. 15.6 mg/10 mL water of bis-hydroxyethyl-1,4-phenylene diamine (5 mM),
2. 7.9 mg/10ml 3A grade alcohol of 2-methyl-1-naphthol (5mM), aqueous buffers at pH 10, 11 and 12 (Chemvelope, American Scientific Products), and
3. 0.1 and 1.0M NaOH.

The buffers and NaOH solutions contained 1% detergent [ethylquad 18/25 methylpolyoxyethylene (15) octadecyl ammonium chloride]. Human blood was diluted with 9 parts water to lyse the cells to provide a hemoglobin concentration in the reaction mixture of about 0.7 g/L. Oxidizers consisted of 0.01M solutions of hydrogen peroxide or diisopropylbenzene dihydroperoxide in 3A alcohol. For a blank containing only air as an oxidant, an aliquot of alcohol containing dihydroperoxide was used as the "oxidant".

The reaction was initiated by mixing 100 μL of the phenylenediamine with 100 μL of the napthol, 50 μL of the lysed blood, 100 μL of oxidant and 700 μL of the buffer or NaOH solution. The adsorbance at 680 nm was measured after 5 minutes using a Hewlett Packard 8450 diode array spectrophotometer. Triplicate measurements were made, the averages of which are reported in Table 1.

TABLE 1

| | Air | $H_2O_2$ | DBDH |
|---|---|---|---|
| pH 10 | 0.2060 | 0.1995 | 0.2915 |
| blank | 0.2449 | 0.1560 | 0.2665 |
| pH 11 | 0.1891 | 0.2876 | 0.5538 |
| blank | 0.2503 | 0.1481 | 0.2616 |
| pH 12 | 0.1866 | 0.4824 | 0.9199 |
| blank | 0.2088 | 0.1117 | 0.2731 |
| 0.1N NaOH | 0.1909 | 0.7417 | 1.0423 |
| blank | 0.1666 | 0.0967 | 0.2048 |
| 1.N NaOH | 0.2576 | 0.6202 | 0.4785 |
| blank | 0.1743 | 0.1381 | 0.1664 |

It can be determined from Table 1 that the reactivity is greatest for the 0.1 N NaOH solution and that the reactivity is far greater with hydrogen peroxide or DBDH present. The reactivity (absorbance for the lysed blood sample minus the blank) increases in the order of air $<H_2O_2<$DBDH.

EXAMPLE II

Experiments were run with high dilutions of blood to determine the sensitivity of the system. The following solutions were prepared:
1. 15.6 mg/10 mL water of bis-hydroxyethyl-1,4-phenylene diamine (5 mM),
2. 7.9 mg/10 mL 3A alcohol of 2-methyl-1-napthol (5 mM) and 0.1 mM NaOH.

Human blood was diluted with 9 parts water to lyse the cells. The oxidizers consisted of 0.1M solutions of hydrogen peroxide and DBDH in 3A alcohol.

The reaction was initiated by mixing 100 μL of the phenylenediamine with 100 μL of the napthol, 10 μL of the lysed blood, 100 μL of oxidant and 700 μL of the NaOH solution. The absorbance at 680 nm was measured after 5 minutes with the results being set out in the following Table 2. The standard deviation of replicates for the blank was 0.02 absorbance units.

TABLE 2

| Blood Dilution | Hb Conc. | $H_2O_2$ | DBDH |
|---|---|---|---|
| Water blank | 0 | 0.1020 | 0.2250 |
| 1 to 100,000 | 0.15 mg/L | 0.1214 | 0.2281 |
| 1 to 30,000 | 0.5 mg/L | 0.1484 | 0.2566 |
| 1 to 10,000 | 1.5 mg/L | 0.2539 | 0.2886 |
| 1 to 3,000 | 5 mg/L | 0.3861 | 0.4870 |
| 1 to 1,000 | 15 mg/L | 0.760 | 1.132 |

From the data of Table 2, it is evident that a dilution of one part of blood in 100,000 of the reaction mixture can be detected with hydrogen peroxide as the oxidant, and one part in 30,000 with DBDH as the oxidant. The greater sensitivity with hydrogen peroxide may be related to the lower blank reading with hydrogen peroxide.

EXAMPLE III

A known indicator system, 0.2 mL of 156 mM tetramethylbenzidine in acetonitrile, was combined with 1.0 ml buffer, (i.e. 120 mM malonic acid pH 5.8), 1.0 mL DBDH in acetonitrile and 1.0 mL hemoglobin in water. The absorbance was measured at 660 nm after five minutes. The results of this experiment are set out in Table 3.

TABLE 3

| Buffer | Hemoglobin | Absorbance |
|---|---|---|
| 120 mM malonic pH 5.8 | 0.mg/dL | 0.000 |
| " | 0.054 | 0.0184 |
| " | 0.081 | 0.0374 |
| " | 0.108 | 0.0574 |
| " | 0.135 | 0.0826 |
| 120 mM + 8.4 mM Fe-HEDTA | 0 | 0.2810 |
| " | 0.135 | 0.4230 |
| 120 mM + 25 mg/dL ascorbate | 0.135 | 0.0000 |
| 120 mM + 25 mg/dL ascorbate | 0 | 0.0000 |
| 0.1N NaOH | 0 | 0.0000 |
| " | 0.135 | 0.0000 |

From Table 3, it can be determined that the sensitivity to hemoglobin at pH 5.8 is very good. However, in the presence of 25 mg/dL ascorbate, the indicator system did not give any color reaction under the test conditions. This indicator system did not produce any color in 0.1N NaOH. The presence of 8.4 mM Fe-HEDTA indicated the presence of hemoglobin when none was present. This indicates that the state of the art indicator system does not detect peroxidase in basic media and that Fe-HEDTA (used to reduce ascorbate interference) can cause false positives due to oxidation of the tetra-methylbenzidine.

EXAMPLE IV

The coupled indicator system of the present invention was tested by preparing a solution of 2.0 mL water, 1.0 L 0.1 N NaOH, 100 μL bis(hydroxyethyl)-1,4-phenylenediamine in water and 100 μL 2-methyl-1-napthol in acetonitrile. Absorbance was measured after five minutes at 560 nm. The results are set out in Table 4.

TABLE 4

| Hemoglobin | Absorbance |
|---|---|
| 0 | 0.11 |
| 0.054 mg/dL | 0.17 |
| 0.81 mg/dL | 0.20 |
| 0.108 mg/dL | 0.23 |
| 0.135 mg/dL | 0.321 |
| 0 + 25 mg/dL ascorbate | 0.068 |

TABLE 4-continued

| Hemoglobin | Absorbance |
| --- | --- |
| 0.135 + 25 mg/dL ascorbate | 0.328 |

The indicator system of the present invention detected hemoglobin with a sensitivity comparable to or greater than the TMB system of Example III without the use of an activator. The presence of 25 mg/dL ascorbate did not significantly affect the ability of this system to detect peroxidase.

What is claimed is:

1. An assay for the detection of a peroxidatively active substance in an aqueous test sample which comprises providing an aqueous medium having a pH of 10 to 14 suspected of containing the peroxidatively active substance to be detected and adding to such medium a peroxide together with a phenylenediamine and a naphthol which, under the conditions of the assay, couple to form a chromogen thereby providing a detectable color change in the medium in the presence of the peroxidatively active substance.

2. The assay of claim 1 wherein the peroxidatively active substance is hemoglobin.

3. The assay of claim 1 wherein the phenylenediamine is selected from the group consisting of

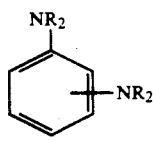

I wherein—NR$_2$ is in position 2 or 4, and

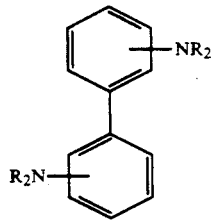

II wherein the—NR$_2$ groups are in positions 4,4'; 4,2'; 2,2' or 5,5' or

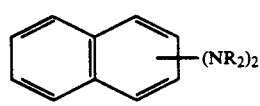

III wherein the—(NR$_2$) groups are in positions 1,2; 1,4; 1,5; 1,7; 2,3; 2,6 or 2,8 where the R groups are independently H, CH$_3$, CH$_2$,CH$_3$, CH$_2$ CH$_2$OH, C$_6$H$_5$ or CH$_2$CH$_2$CH$_3$ wherein the aromatic rings are substituted with 0 to 5 X groups wherein X is independently H, Cl, NO$_2$ Br, I, Fl, CN, CH$_3$, CH$_2$CH$_3$, CH$_2$CH$_2$CH$_3$, OCH$_3$, OCH$_2$CH$_3$ or C$_6$H$_5$ and the naphthol has the formula:

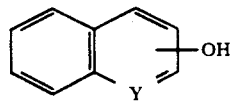

wherein y is CX, S, 0 or N and is either ortho or meta to the carbon atoms bridging the aromatic rings and wherein the aromatic rings are independently substituted with 0 to 7 X groups where X is H, Cl, Bn, I, Fl, CN, CH$_3$, CH$_2$CH$_3$, CH$_2$CH$_2$CH$_3$, OCH$_3$, OCH$_2$CH$_3$, SO$_3$H, CO$_2$H, PO$_3$H or C$_6$H$_5$.

4. The assay of claim 3 wherein the phenylenediamine is

Structure I: bis-hydroxyethyl-1,4-phenylenediamine; 1,2 phenylenediamine, 1,4-phenylenediamine hydrochloride; 3-nitro-1,2-phenylenediamine; 4-nitro-1,2-phenylenediamine; 4-methoxy-1,2-phenylenediamine; 2-chloro-1,4-phenylenediamine sulfate; 2-ethoxy-1,4-phenylenediamine; N,N-dimethyl-1,4-phenylenediamine; 2,3-dimethyl-1,4-phenylenediamine; 4,5-dimethyl-1,2-phenylenediamine; N,N-diethyl-1,4-phenylenediamine dihydrochloride; N-phenyl-1,4-phenylenediamine; N,N,N',N'-tetramethyl-1,4-phenylenediamine; N-methyl-N'-hydroxyethyl-1,4-phenylenediamine; or 2,3,5,6-tetramethyl-1,4-phenylenediamine;

Structure II: 3,3',5,5'-tetramethyl-benzidine; 2,2'-dimethylbiphenyl-4,4'-diamine; 3,3'-diaminobenzidine-tetrahydrochloride; or N,N,N',N'-tetramethyl-biphenyl-4,4'diamine;

Structure III: N,N-dimethyl-1,4-naphthyldiamine; 1,4-naphthyldiamine; 1,5-diaminonaphthalene; 1,8-diaminonaphthalene; 2,3-diaminonaphthalene; 5-chloro-1,4-naphthyldiamine or 1-ethoxy-2,3-diaminonaphthalene; and the naphthol is 2-methoxy-1-naphthol; 2-methyl-1-naphthol; 1-naphthol, 2-naphthol, 4-chloro-1-naphthol; 1-bromo-2-naphthol; 6-bromo-2-naphthol; 1,6-dibromo-2-naphthol; 2,4-dichloro-1-naphthol; 6-methyl-2-naphthol; 1-methoxy-2-naphthol; 2-phenyl-1-naphthol; 1-hydroxy quinoline, 5-hydroxy quinoline; 3-hydroxy-1-methyl-quinoline; 6-hydroxy quinoline; 2-hydroxy quinoline, 8-hydroxyquinoline-5-sulfonic acid; 1-naphthol-4-carboxylic acid; 8-hydroxyl-5-nitroquinoline; 5-chloro-8-hydroxyquinoline or 4-ethyl-1-naphthol.

5. The assay of claim 1 wherein the color forming combination comprises bis-hydroxyethyl-1,4-phenylenediamine and 2-methyl-1-naphthol.

6. An assay for the detection of hemoglobin in an aqueous test sample having a pH of from 10 to 14 which comprises the steps of adding to an aqueous medium suspected of containing hemoglobin, a peroxide together with a phenylenediamine and a naphthol which, under the conditions of the assay, couple to form a chromogen when hemoglobin is present thereby providing a detectable color change in the medium.

7. The assay of claim 6 wherein the color forming combination comprises bis-hydroxyethyl-1,4-phenylenediamine and 2-methyl-1-naphthol.

* * * * *